United States Patent
Newman et al.

(10) Patent No.: US 6,376,715 B1
(45) Date of Patent: Apr. 23, 2002

(54) PROCESS FOR THE PREPARATION OF BISPHOSPHINES

(75) Inventors: Paul David Newman, Cardiff; Richard Anthony Campbell, Fife; Robert Paul Tooze, Cleveland; Graham Ronald Eastham, Durham; Jamie Michael Thorpe, Cleveland; Peter Gerald Edwards, Cardiff, all of (GB)

(73) Assignee: Ineos Acrylics U.K. Limited, Hampshire (GB)

( * ) Notice: Subject to any disclaimer, the term of this patent is extended or adjusted under 35 U.S.C. 154(b) by 0 days.

(21) Appl. No.: 09/646,049

(22) PCT Filed: Mar. 16, 1999

(86) PCT No.: PCT/GB99/00797

§ 371 Date: Dec. 1, 2000

§ 102(e) Date: Dec. 1, 2000

(87) PCT Pub. No.: WO99/47528

PCT Pub. Date: Sep. 23, 1999

(30) Foreign Application Priority Data

Mar. 16, 1998 (GB) ............................................. 9805348

(51) Int. Cl.$^7$ ................................................. C07F 9/50
(52) U.S. Cl. .......................................................... 568/17
(58) Field of Search ............................. 568/13, 17, 16; 502/162

(56) References Cited

U.S. PATENT DOCUMENTS 4,879,008 A * 11/1989 Puckette

FOREIGN PATENT DOCUMENTS

| DE | 41 34 772 | 5/1992 | | |
|---|---|---|---|---|
| GB | 877 592 | 9/1961 | | |
| WO | 96 17856 | 6/1996 | | |
| WO | 96 19434 | 9/1996 | | |
| WO | WO99/09040 | * 2/1999 | ............. | C07C/9/50 |

OTHER PUBLICATIONS

J Am. Chem. Soc. by Boris Rybtchinski et al vol. 118, pp. 12406–12415, 1996.*
Organometallics by Mark Gandelman et al vol. 16, pp. 3981–3986, 1997.*
Chem. Commun. by Milko van der Boom et al pp. 917–918, 1998.*
J Am. Chem. Soc. by Miko van der Boom et al vol. 120 pp. 13415–13421, 1998.*

* cited by examiner

*Primary Examiner*—Jean F. Vollano
(74) *Attorney, Agent, or Firm*—Pillsbury Winthrop LLP

(57) ABSTRACT

A method of manufacturing a compound of general formula $(R_3—C)_2P—L^1—X—L^2—P—(C—R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorus atom to the group X and X is a bridging group comprising an optionally substituted aryl moiety to which the phosphorus atoms are linked on available adjacent carbon atoms, comprises: i) reacting together a compound of formula $H—L^1—X—L^2—H$ with an organometallic compound to form an intermediate compound of formula $M—L^1—X—L^2—M$, where M is an alkali metal atom; ii) reacting said intermediate compound with a compound of formula $(R_3—C)_2P—A$, where A is a halogen atom, to form said compound of general formula $(R_3—C)_2P—L_1—X—L^2—P—(C—R_3)_2$, M is preferably lithium, potassium or sodium and the intermediate compound may be isolated or not. The reaction (i) may advantageously be carried out in the presence of a complexing agent such as tetramethyethylenediamine.

9 Claims, No Drawings

PROCESS FOR THE PREPARATION OF BISPHOSPHINES

This application is the national phase of PCT/GB99/00797, filed Mar. 16, 1999, now WO 99/47528.

The present invention relates to a phosphine compound which is useful as a component of a catalyst system which may be used in the carbonylation of olefins, and in particular to a method of manufacturing such phosphine compounds.

WO 96/19434 discloses a process for the carbonylation of ethylene and a catalyst system for use therein. The catalyst system described in that document comprises a bidentate phosphine of general formula $(R_3—C)_2P—L^1—X—L^2—P—(C—R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorus atom to the group X and X is a bridging group comprising an optionally substituted aryl moiety to which the phosphorus atoms are linked on available adjacent carbon atoms. One example of such a bidentate phosphine is bis(di-$^t$butyl phosphino)-o-xylene (also known as 1,2,bis(di-t-butylphosphinomethyl)benzene).

Such catalysts may be made by mixing the phosphine ligand with a suitable source of palladium such as palladium acetate. WO 96/19434 describes the preparation of one form of the ligand via the phosphonium salt produced from the reaction of the appropriate secondary phosphine with the corresponding aromatic dihalide. In the preferred form of the phosphine ligand in WO 96/19434, R is a lower alkyl group, in particular methyl. A problem with manufacturing this ligand by the route described is that the secondary phosphine which is used (e.g. di-$^t$butyl phosphine) is toxic, highly reactive, smelly and flammable. We have also found that the reaction is low yielding and converts some of the di-$^t$butyl phosphine to a non-reclaimable waste product which must be disposed of.

Al-Salem et al in Journal of the Chemical Society (Dalton) 1979 page 1980 describes making 1,5 bis(di-t-butylphosphino)pentane by reacting lithium metal with 1,5-dibromopentane and then phosphorylating the resulting lithiated intermediate with t-butylchlorophosphine. This method, for forming a phosphine of an alkyl compound, starts from the halogenated alkyl compound. Alkyl halides typically require considerable care during storage and use and may be very unpleasant to use. Therefore using this method of making the phosphine using the non-halogenated alkyl compound as a starting material would require an extra step of converting first to the alkyl halide.

We have now found that phosphine ligands of the type described in WO 96/19434 may be prepared by a high yielding route using more benign materials which produce less waste phosphorus product than the route described in WO 96/19434.

According to the invention, a method of manufacturing a compound of general formula $(R_3—C)_2P—L^1—X—L^2—P—(C—R_3)_2$ in which each R is independently a pendant, optionally substituted, organic group through which the group is linked to tertiary carbon atom C; $L^1$, $L^2$ are independently a linking group selected from an optionally substituted lower alkylene chain connecting the respective phosphorus atom to the group X and X is a bridging group comprising an optionally substituted aryl moiety to which the phosphorus atoms are linked on available adjacent carbon atoms comprises the steps of i) reacting together a compound of formula $H—L^1—X—L^2—H$ with an organometallic compound to form an intermediate compound of formula $M—L^1—X—L^2—M$, where M is an alkali metal atom, ii) reacting said intermediate compound with a compound of formula $(R_3—C)_2P—A$, where A is a halogen atom, to form said compound of general formula $(R_3—C)_2P—L^1—X—L^2P—(C—R_3)_2$.

The compound of general formula $(R_3—C)_2P—L^1—X—L^2—P—(C—R_3)_2$ may be useful as a component of a catalyst compound. In particular WO 96/19434 describes the use of such compounds as bidentate ligands which, when used together with a Group VIII metal such as palladium are effective catalysts for the carbonylation of olefins.

The pendant, optionally substituted organic groups, R may be independently selected from a wide range of components. Preferably, the pendant groups are optionally substituted lower alkyl, e.g. $C_{1-8}$, and may be branched or linear.

Particularly preferred is when the organic groups, R, when associated with their respective carbon atom, form composite groups which are at least as sterically hindering as tert-butyl. Steric hindrance in this context is as discussed at page 14 et seq of "Homogeneous Transition Metal Catalysis—A Gentle Art", by C Masters, published by Chapman and Hall, 1981. In one preferred embodiment, the organic groups R are all methyl groups, i.e. a preferred form of $R_3$—C group is a tertiary butyl group.

The linking groups, $L^1$ and $L^2$, are independently selected from an optionally substituted, particularly lower alkylene, e.g. $C_1$ to $C_4$, substituted, lower alkylene, e.g. $C_1$ to $C_4$ chain. Especially preferred is when both $L^1$ and $L^2$ are methylene.

The bridging group X is, preferably, an aryl moiety, e.g. a phenyl group, which may be optionally substituted, provided that the two phosphorus atoms are linked to adjacent carbon atoms, e.g. at the 1 and 2 positions on the phenyl group. Optional substitution of the aryl moiety may be by other organic groups, e.g. alkyl, particularly $C_{1-8}$, aryl, alkoxy, carbalkoxy, halo, nitro, trihalomethyl and cyano. Furthermore, the aryl moiety may be a fused polycyclic group, e.g. naphthalene, biphenylene or indene.

Examples of compounds which may advantageously be made by the method according to the invention are bis(di-tert-butyl phosphino)-o-xylene (also known as 1,2 bis(di-tert-butylphosphinomethyl)benzene), bis(di-t-neopentyl phosphino)-o-xylene and bis 1,2 (di-tert-butyl phosphino) naphthalene.

The reaction of a compound of formal $H—L^1—X—L^2—H$ with a basic organometallic compound of formula $R'''M$ to form an intermediate compound of formula $M—L^1—X—L^2—M$, where M is an alkali metal atom, may be carried out by various means which are known in the art of organometallic chemistry. For example, such metallation methods are described by Wilkinson et al. in "Comprehensive Organometallic Chemistry" at page 54; and by Lambert et al. in "Preparative Polar Organometallic Chemistry".

The organometallic compound may comprise a compound of formula $R'''—M$, where $R'''$ is an organic group which tends to withdrawn electrons from the metal atom M. Suitable organic groups include aromatic or aliphatic groups, especially alkyl groups, which may be substituted. Lower alkyl groups have been found to be particularly suitable, for example preferred $R'''$ compounds include n-butyl, t-butyl, sec-butyl, methyl or pentyl. M may be any suitable alkali metal which forms a polar organometallic group with $R'''$. Suitable metals include those of Group IA, e.g. sodium, potassium or lithium. When M comprises K or NA the $R'''—M$ metallating agent is preferably generated in situ by an exchange mechanism, e.g. by the reaction between $R'''$—Li and potassium or sodium t-butoxide as described by Lochman et al. in Tetrahedron Letter No. 2 pages 257–262 (1966). Preferred metallating compounds are butyl lithium, butyl sodium and butyl potassium, the latter compounds preferably being formed in situ by the reaction of butyl lithium with potassium or sodium t-butoixde.

Alternative organometallic compounds are also known in the art and may comprise $Me_3SiCH_2K$, alkali amides $MNH_2$ preferably used in liquid ammonia, lithium dialkylamides e.g. lithium diisopropylamide (LDA), lithium, sodium or potassium metals, metal hydrides e.g. KH in the presence of coordinating compounds.

The reaction between $R'''M$ and $H—L^1—X—L^2—H$ may be carried out in the presence of a solvent. Any solvent used must not contain any component which reacts with the intermediate compound, and suitable such solvents will be well known to the skilled chemist. Favoured solvents include dry alkyl ethers e.g. diethyl ether, methyl t-butyl ether, di(n-propyl)ether; tetrahydrofuran(THF), and hydrocarbons such as hexane and heptane.

The reaction between $R'''M$ and $H—L^1—X—L^2—H$ may be beneficially carried out in the presence of a basic compound which is capable of forming a complex with the metal. A preferred complexing agent is tetramethylethylenediamine(TMEDA). The presence of TMEDA is greatly preferred when the metallating agent is alkyl lithium or alkyl sodium. When alkyl potassium (or alkyl lithium/potassium t-butoxide mixture) is used, we have found that the reaction proceeds satisfactorily in the absence of TMEDA.

The mole ratios of metallating agent:$H—L^1—X—L^2—H$ are preferably in the range 1:1 to 10:1, more preferably at least 1.5:1. The preferred ratio depends upon the nature of the metallating agent used, for example when alkyl lithium is used a ratio of $R—Li:H—L^1—X—L^2—H$ of 3:1 may be preferred. Higher ratios may be preferred to encourage the formation of di-substituted product rather than mono-substituted compounds.

A preferred ratio of $R'''M$:complexing agent is in the range 1:1–4:1, especially preferred is a ratio of about 1:1 to about 2:1.

It is preferred to conduct the metallation reaction between $R'''M$ and $H—L^1—X—L^2—H$ at a temperature in the range −20 to 150° C., more preferably at room temperature or above. The optimum temperature and reaction time depends upon the identity of the reactants, in particular upon the alkali metal which is used. For example we have found, using o-xylene as the compound to be metallated that when alkyl lithium is used, the reaction proceeds well at room temperature (i.e. about 20–22° C.) whereas reactions using alkyl sodium and potassium are preferably conducted at about 60, (e.g. 50–70° C.) and about 80° C. (e.g. 70–90° C.) respectively. The intermediate compound, $M—L^1—X—L^2—M$ may be isolated from the reaction mixture prior to conducting the reaction between $M—L^1—X—L^2—M$ and the compound of formula $(R_3—C)_2P—A$. However isolation of the intermediate may not be necessary and the reaction has been found to proceed very satisfactorily when the intermediate is not isolated. When the intermediate product $M—L^1—X—L^2—M$ can be separated relatively easily, for example if it is in a different physical form from the starting materials, then it may be advantageous to isolate the intermediate form the reaction mixture to encourage the formation of more intermediate. We have found that the reaction mixture may contain partially reacted compounds of formula $M—L^1—X—L^2—H$ which may be reacted to completion by the addition of further quantities of $R'''M$ and complexing agent if used.

The phosphorylation reaction between the intermediate product $M—L^1—X—L^2—M$ and the halophosphine $(R_3—C)_2P—A$ is also carried out in the presence of a solvent and similar solvents to those used for the metallation are suitable, e.g. ethers, C5+ alkanes and petroleum ethers. We have found that, when the metal used is potassium, the reaction is favoured when diethyl ether is used as a solvent for the phosphorylation reaction, although an alkane e.g. heptane, may be preferred for the metallation reaction. Also, even when sodium or lithium is used as the metal species, it may be beneficial to use a different solvent for the phosphorylation from that used for the metallation, e.g. to enable higher temperatures to be used in one reaction yet allow an easy separation of the solvent from the product of the second reaction.

The phosphorylation reaction may be conducted at elevated temperatures, e.g. at temperatures of 60° C. or greater, but it is preferred to conduct the reaction at room temperature or below, e.g. at −20 to 25° C.

The compound of general formula $(R_3—C)_2P—L^1—X—L^2—P—(C—R_3)_2$ may be isolated from the reaction mixture by distilling off the excess solvent, preferably under vacuum and then extracting the product compound into a solvent, e.g. methanol, from which it may be precipitated.

The invention will be further described, by way of example only, below. In all reactions, the reactants and apparatus used were prepared to allow the reaction to proceed in anhydrous and anaerobic reaction conditions.

EXAMPLE 1

N,N,N',N'-Tetramethylethylenediamine (0.79 $cm^3$, 5.25 mmol) was added to a stirred solution of n-butyllithium (2.10 $cm^3$, 2.5M in hexane, 5.25 mmol) in heptane (15 $cm^3$) under an atmosphere of nitrogen. After five minutes, ortho-xylene (0.26 $cm^3$, 2.10 mmol) was added slowly. A orange-brown precipitate formed after leaving the solution stirring at room temperature for 96 hours.

Di-tert-butylchlorophosphine (1.40 $cm^3$, 7.37 mmol) was added, then at room temperature the solution was left to stir until the colour disappeared.

A sample of the reaction mixture was analysed by $^{31}P\{^1H\}$ NMR and the conversion to bis(di-tert-butyl phosphino)-o-xylene and to the mono-substituted analogue, was determined. The results are shown in Table 1.

EXAMPLES 2–8

The experimental procedure of Example 1 was repeated but varying the reactant ratios and reaction conditions as shown in Table 1.

EXAMPLE 9

The experimental procedure described above was repeated using a ratio of butyllithium:TMEDA:o-xylene of 4:4:1, a temperature of 25° C. and a reaction time of 48 hrs, but the product of the reaction between the butyl lithium and o-xylene/TMEDA was filtered to separate the brown solid from the red liquid. Each was then reacted separately with dibutychlorophosphine and the conversion to bis(di-tert-butyl phosphino)-o-xylene and to the mono-substituted analogue, was determined. The results are shown in Table 2.

EXAMPLES 10–13 n-Butyllithium (11 mmol) was added dropwise to a well-stirred solution of o-xylene (0.6 ml, 5 mmol) and potassium tert-butoxide (1.2g 11 mmol) in heptane (25 ml). The reactions were stirred (and sometimes heated) for a predetermined length of time (see Table 3).

The system was cooled by placing it in an ice bath and di-tert-butylchlorophosphine (1.87 ml, 11 mmol) was then slowly added to the flask. The system was allowed to stir until all of the colour had disappeared. Diethyl ether (50 cm$^3$) was added to the flask to ensure that all of the phosphines produced were dissolved. A sample of the resulting solution was collected is a sealed NMR tube and analysed by $^{31}$P {$^1$H} NMR.

TABLE 1

| Example | Ratio butyllithium: TMEDA: o-xylene | T ° C. | time (hrs) | % conversion to disubstituted product (re: o-xylene) | ratio di: mono product |
|---|---|---|---|---|---|
| 1 | 2:2:1 | 25 | 96 | 32 | 0.7 |
| 2 | 2.5:2.5:1 | 25 | 96 | 31 | 0.77 |
| 3 | 2.5:2.5:1 | 60 | 12 | 32 | 1.60 |
| 4 | 2.5:2.5:1 | 40 | 6 | 39 | 1.08 |
| 5 | 2.5:2.5:1 | 60 | 6 | 34 | 0.85 |
| 6 | 3:2:1 | 60 | 6 | 57 | 1.50 |
| 7 | 4:4:1 | 25 | 96 | 57 | 1.86 |
| 8 | 4:2:1 | 25 | 96 | 69 | 2.3 |

TABLE 2

|  | % conversion (mono) | % conversion (di) |
|---|---|---|
| solid | 5 | 38 |
| liquid | 30 | 8 |

TABLE 3

| Example | Ratio BuLi/BuOK/ Xylene | Potassiation reaction time and temperature (° C.) | % Conversion di substituted product |
|---|---|---|---|
| 10 | 2.2:2.2:1 | 1 hour, room temp. (RT) | 40 |
| 11 | 3:3:1 | 1 hour at RT + 1 hr @ 60° C. | 45 |
| 12 | 2.2:2.2:1 | 1 hour @ 80° C. | 44 |
| 13 | 3:3:1 | 1 hour @ 80° C. | 49 |

EXAMPLE 14

O-xylene (3.3 cm$^3$, 270×10$^{-2}$ mol) was added by syringe to a suspension of potassium t-butoxide (6.6 g, 5.88×10$^{-2}$ mol) in 40/60 petroleum ether (150 cm$^3$). 42 cm$^3$ of a 1.4 M solution of butyl lithium in hexane was added to the ether mixture, with cooling. The mixture was stirred overnight to complete the reaction which resulted in an orange-red solid which was the dipotassio-o-xylene. The mixture was filtered and the solid washed with further petroleum ether.

The dipotassio derivative was then suspended in diethyl ether (150 cm$^3$) at −78° C. and di-t-butylchlorophosphine (10 g, 5.54×10$^{-2}$ mol) was added by syringe. The mixture was stirred for an hour, brought slowly to room temperature and then filtered. The filtrate was hydrolysed by addition of 1 cm$^3$ of degassed water and dried. The yield (based on o-xylene) was 94%. Analysis by $^{31}$P {$^1$H} NMR showed that the yield of α,α$^1$bis(dit-butylphosphino)o-xylene was 80%, whilst that of the monophosphine was 10%.

EXAMPLE 15

Potassium-tert-butoxide (3.99 g, 35.6 mmol), heptane (150 cm$^3$) and oxylene (1.47 cm$^1$, 12 mmol) were added to a 500 ml round bottomed flask. To this stirred solution n-butyllithium (14.45 cm$^3$, 36.1 mmol, 2.5M in hexane) was added slowly and the flask heated to 80° C. for 1 hour. An orange/red precipitate formed which was separated by filtration and washed with pentane (3×100 cm$^3$) before being resuspended in diethyl ether (100 cm$^3$) which had been pre-cooled to −20° C. To this solution maintained at −20° C. was added di-t-butylchlorophosphine (4.58 cm$^3$, 24.1 mmol) and the reaction allowed to warm to room temperature before being stirred overnight. The in-situ reaction yield of α,α$^1$bis(dit-butylphosphino)o-xylene as determined by $^{31}$P NMR was 64%.

EXAMPLE 16

The reaction described in Example 15 was repeated except that the orange-red precipitate of dipotassio-o-xylene was resuspended in 100 cm of diethyl ether which had been pre-cooled to 0° C. and the solution was maintained at 0° C. while di-t-butylchlorophosphine (4.58 cm$^3$, 24.1 mmol) was added. The reaction was allowed to warm to room temperature before being stirred overnight. The in-situ reaction yield of α,α$^1$bis(dit-butylphosphino)o-xylene as determined by $^{31}$NMR was 74.9%.

EXAMPLE 17

The reaction described in Example 15 was repeated except that the orange-red precipitate of dipotassio-o-xylene was resuspended in 100 cm of diethyl ether at room temperature and the solution was maintained at room temperature while di-t-butylchlorophosphine (4.58 cm$^3$, 24.1 mmol) was added. The reaction was stirred overnight. The in-situ reaction yield of α,α$^1$bis(dit-butylphosphino)o-xylene as determined by $^{31}$P NMR was 75.5%.

EXAMPLE 18

Sodium-tert-butoxide (17.29 g, 180 mmol), N,N,N',N'-Tetramethylethylenediamine (27.1 cm$^3$, 180 mmol), heptane (100 cm$^3$) and o-xylene (7.32 cm$^3$, 60 mmol) were added to a 1 liter round bottomed flask. To this stirred solution n-butyllithium (72.0 cm$^3$, 180 mmol, 2.5M in hexane) was added slowly and the flask heated to 60° C. for 2 hours. An orange precipitate formed which was separated by filtration and washed with pentane (100 cm$^3$) before being resuspended in pentane (100 cm$^3$). To this was added di-t-butylchlorophosphine (22.75 cm$^3$, 120 mmol) and the reaction stirred at room temperature overnight. The reaction was quenched by the addition of degassed/deionised water (50 cm$^3$) when two clear layers formed and the pentane layer (upper layer) was isolated. The solvent was removed in-vacuo and the product purified by washing with cold methanol (−10 C). Yield (20.0 g, 84.6%).

What is claimed is:
1. A method of manufacturing a compound of formula (I)

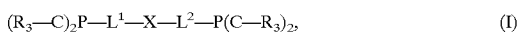

in which each R is, independently, a pendant, optionally substituted, organic group through which the group is linked to tertiary carbon atom C;

L$^1$, L$^2$ are, independently, a linking group selected from an optionally substituted C$_1$ to C$_4$ alkylene chain connecting the respective phosphorus atom to the group X, and X is a bridging group comprising an optionally substituted aryl moiety to which the phosphorus atoms are linked on available adjacent carbon atoms comprising:

i) reacting together a compound of formula $$H-L^1-X-L^2-H$$

with an organometallic compound to form an intermediate compound of formula $$M-L^1-X-L^1-M,$$

where M is an alkali metal atom, and ii) reacting said intermediate compound with a compound of formula $$(R_3-C)_2P-L^1-X-L^2-P(C-R_3)_2.$$

2. A method as claimed in claim 1, wherein M is sodium, potassium or lithium.

3. A method as claimed in claim 2, wherein the organometallic compound is a compound of formula $R'''-M$, where $R'''$ is an organic group which withdraws electrons from the metal atom M.

4. A method as claimed in claim 1, wherein the organometallic compound is a compound of formula $R'''-M$, where $R'''$ is an organic group which withdraws electrons from the metal atom M.

5. A method as claimed in claim 1, wherein $R'''-M$ is generated in situ by an exchange reaction between $R'''-Li$ and potassium or sodium alkyl oxide.

6. A method as claimed in claim 1, wherein the reaction between $R'''-M$ and $H-L^1X-L^2-H$ is carried out in the presence of a basic compound which is capable of forming a complex with the metal.

7. A method as claimed in claim 6, wherein said basic compound comprises tetramethylenediamine.

8. A method as claimed in claim 1, wherein said compound of formula (I) is selected from the group consisting of α,α'bis(di-t-butylphosphino)-o-xylene, bis(di-t-neopentylphosphino)-o-xylene or bis-1,2-(di-t-butylphosphino)naphthalene.

9. A catalyst suitable for catalyzing the carbonylation of ethylene comprising a compound of formula $(R_3-C)_2P-L^1-X-L^2-P(C-R_3)_2$, prepared by a method as claimed in claim 1, and palladium or a compound thereof.

* * * * *

UNITED STATES PATENT AND TRADEMARK OFFICE
CERTIFICATE OF CORRECTION

PATENT NO. : 6,376,715 B1
DATED : April 23, 2002
INVENTOR(S) : Newman et al.

It is certified that error appears in the above-identified patent and that said Letters Patent is hereby corrected as shown below:

<u>Column 7,</u>
Line 11, following "ii) reacting said intermediate compound with a compound of formula", please insert -- $(R_3-C)_2P-A$, where A is a halogen atom, to form said compound of formula --.

Signed and Sealed this

Seventeenth Day of September, 2002

Attest:

Attesting Officer

JAMES E. ROGAN
*Director of the United States Patent and Trademark Office*